United States Patent [19]

Franko et al.

[11] 4,163,790
[45] Aug. 7, 1979

[54] METHOD FOR INCREASING CORONARY BLOOD FLOW IN MAMMALS

[75] Inventors: Bernard V. Franko; Anthony G. Proakis, both of Richmond, Va.

[73] Assignee: A. H. Robins Company, Inc., Richmond, Va.

[21] Appl. No.: 886,486

[22] Filed: Mar. 14, 1978

Related U.S. Application Data

[63] Continuation-in-part of Ser. No. 795,846, May 11, 1977, abandoned.

[51] Int. Cl.² ............... A61K 31/445; A61K 31/535
[52] U.S. Cl. .............................. 424/267; 424/248.56
[58] Field of Search ........................ 424/267, 248.56

[56] References Cited

U.S. PATENT DOCUMENTS

| | | | |
|---|---|---|---|
| 3,806,526 | 4/1974 | Carr et al. | 424/267 |
| 3,852,455 | 12/1974 | Carr | 424/267 |
| 3,922,276 | 11/1975 | Duncan et al. | 424/267 |
| 3,931,197 | 1/1976 | Carr et al. | 424/267 |
| 3,946,022 | 3/1976 | Carr et al. | 424/267 |
| 3,956,296 | 5/1976 | Duncan et al. | 544/130 |

OTHER PUBLICATIONS

Chem. Abst. 72, 100535(h), 1970–Duncan et al.

Primary Examiner—Albert T. Meyers
Assistant Examiner—D. W. Robinson

[57] ABSTRACT

Compounds of the following general formula are useful for increasing coronary blood flow in mammals:

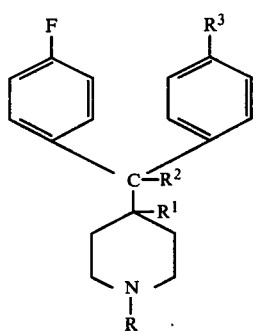

wherein R is hydrogen, acetyl, p-fluorobenzoylpropyl, carbamoyl, N-methylcarbamoyl, N,N-dimethylcarbamoyl, phenylcarbamoyl, or N-(ω-morpholinoethyl)carbamoyl; $R^1$ is hydrogen; $R^2$ is hydrogen or hydroxy; or $R^1$ and $R^2$ taken together form a second bond between the carbon atoms bearing $R^1$ and $R^2$; $R^3$ is hydrogen or fluorine and pharmaceutically acceptable acid addition salts thereof.

7 Claims, No Drawings

METHOD FOR INCREASING CORONARY BLOOD FLOW IN MAMMALS

The present application is a continuation-in-part application of copending application Ser. No. 795,846 filed May 11, 1977 now abandoned.

BACKGROUND OF THE INVENTION

1. Field of Invention

The present invention relates to methods for increasing coronary arterial blood flow in mammals with a minimum of undesirable side effects using certain 1-R-4-(α-substituted or α,α-disubstituted)-p-fluorobenzylpiperidines and 1-R-4-(α-substituted)-p-fluorobenzylidenepiperidines.

2. Description of the Prior Art

Nitroglycerin has been used extensively as a vascular dilator in the treatment of angina pectoris. Although it increases coronary blood flow, its duration of effectiveness is short. When the dosage is increased to lengthen duration, hypotension results. A longer acting vasodilator, lidoflazine, 4-[4,4-bis(4-fluorophenyl)butyl]-N-(2,6-dimethylphenyl)-1-piperazine acetamide is disclosed in U.S. Pat. No. 3,267,104, and the The Merck Index, 9th Ed., p. 5324.

U.S. Pat. No. 3,956,296 discloses certain 1-R-4-(α-substituted and α,α-disubstituted)-p-fluorobenzylpiperidines and methods for their preparation, said compounds having anti-inflammatory, sedative and tranquilizer activities. U.S. Pat. No. 3,922,276 discloses certain 1-R-4-(α-substituted)-p-fluorobenzylidenepiperidines and methods for their preparation, said compounds having anti-secretory and central nervous system stimulating activities.

SUMMARY OF INVENTION

The present invention is concerned with methods for increasing coronary arterial blood flow in mammals using compounds of the following general formula:

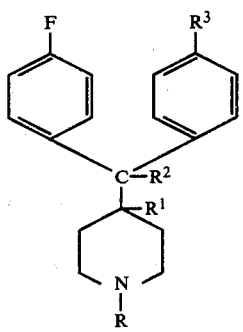

Formula I wherein;
R is hydrogen, acetyl, p-fluorobenzoylpropyl, carbamoyl, N-methylcarbamoyl, N,N-dimethylcarbamoyl, phenylcarbamoyl, or N-(ω-morpholinoethyl)carbamoyl;
$R^1$ is hydrogen;
$R^2$ is hydrogen or hydroxy; or
$R^1$ and $R^2$ taken together form a second bond between the carbon atoms bearing $R^1$ and $R^2$;
$R^3$ is hydrogen or fluorine, and
pharmaceutically acceptable acid addition salts thereof.

The compounds represented by the foregoing Formula I have been shown to increase coronary arterial blood flow in anesthetized dogs with minimal side effects. In particular, there was less peripheral vasodilation than that exhibited by nitroglycerin or adenosine. The increased coronary blood flow is prolonged when compared to comparable doses of nitroglycerine or adenosine. The compounds of Examples 1 and 2 represent preferred compounds of the present invention.

The compounds useful in practicing the present invention are set forth hereinbelow. For a more complete description of the compounds and their preparation, the disclosures of Duncan and Boswell U.S. Pat. Nos. 3,956,296 and 3,922,276 are hereby incorporated by reference as fully as though set forth herein.

| Ex. No. | Name of Compound |
|---|---|
| 1 | 1-[3-(p-fluorobenzoyl)propyl]-4-[α-(p-fluorophenyl)-α-hydroxy]-p-fluorobenzylpiperidine oxalate. |
| 2 | 1-[3-(p-fluorobenzoyl)propyl]-4-[α-(p-fluorophenyl)]-p-fluorobenzylpiperidine. |
| 3 | 4-[α-(p-fluorophenyl)-α-hydroxy]-p-fluorobenzylpiperidine hydrochloride hemihydrate. |
| 4 | 1-acetyl-4-[α-(p-fluorophenyl)-α-hydroxy]-p-fluorobenzylpiperidine. |
| 5 | 4-[α-(p-fluorophenyl)-α-hydroxy]-p-fluorobenzylpiperidine-1-carboxamide. |
| 6 | 4-[α-(p-fluorophenyl)-α-hydroxy]-p-fluorobenzylpiperidine-1-carboxanilide. |
| 7 | 4-[α-(p-fluorophenyl)]-p-fluorobenzylpiperidine oxalate. |
| 8 | 1-(N-methyl)-4-[α-(p-fluorophenyl)]-p-fluorobenzylpiperidine-1-carboxamide. |
| 9 | 1-acetyl-4-(α-phenyl-α-hydroxy)-p-fluorobenzylpiperidine. |
| 10 | 4-[α-(p-fluorophenyl)]-p-fluorobenzylidenepiperidine hydrochloride. |
| 11 | 4-(α-phenyl)-p-fluorobenzylidenepiperidine. |
| 12 | N,N-dimethyl-4-[α-(p-fluorophenyl)]-p-fluorobenzylpiperidine-1-carboxamide. |
| 13 | N-(ω-morpholinoethyl)-4-[α-(p-fluorophenyl)]-p-fluorobenzylpiperidine-1-carboxamide. |

The procedure used to determine the effect of the aforementioned compounds on coronary arterial blood flow is described as follows.

Mongrel dogs of either sex were anesthetized with phenobarbital sodium (100 mg/kg) and pentobarbital sodium (100 mg. total dose). The trachea was surgically exposed, a tracheal tube was inserted and the dog was artificially respired with room air using a Harvard Model 613 Respirator. The left carotid artery was exposed, cannulated and connected to a Statham P23AC Strain Gauge Transducer for measuring peripheral blood pressure. The heart was exposed by a left thoracotomy at the fourth intercostal space. An approximately 1.5 cm. segment of the left anterior descending coronary artery was exposed and a Statham electromagnetic blood flow probe was implanted around the vessel. The flow probe cable was connected to a Statham Model 2201 Blood Flow Meter. A second blood flow probe was placed around an exposed femoral artery for monitoring changes in peripheral blood flow. Continuous recordings of carotid arterial blood pressure, and of femoral and coronary arterial blood flows, were obtained using a Grass Model 5 Polygraph.

The compounds were administered via a femoral vein. Changes in both magnitude and duration of change in coronary blood flow from pre-drug levels were determined. Generally, multiple doses of the compounds tested were administered to a single dog. Appropriate intervals between doses were allowed to permit the blood flow to return to control levels.

The magnitude and duration of increased coronary arterial blood flow was measured for Examples 1 and 2 and the reference compounds, nitroglycerin and adenosine. Immediately after intravenous injection, each compound produced an increase of coronary arterial blood flow that was slight to pronounced depending on the dose. Durations of effects were determined as the times required for both 50% and 100% reduction of the compound-induced increases of coronary blood flow. Data for compounds of Examples 1 and 2 are given in Tables 1 and 2 respectively. Data for nitroglycerin and adenosine are given in Tables 3 and 4 respectively. Experimental compounds of Examples 1 and 2 v. reference compounds are delineated clearly when considering duration of the second phase of the response which is reflected in the time for 100% decay (complete return to the pre-treatment level). The data show a superiority of the compounds of Examples 1 and 2 over nitroglycerin and adenosine. Doses in the milligram range were used for compounds of Examples 1 and 2, whereas microgram doses of the reference compounds were given. Higher doses of nitroglycerine and adenosine produce hypotension. The distinct advantage of less peripheral vasodilation was noted with the compounds of Examples 1 and 2 as determined by changes in blood flow in the femoral artery.

TABLE 1

The Effect of 1-[3-(p-fluorobenzoyl)propyl]-4-[α-(p-fluorophenyl)-α-hydroxy]-p-fluorobenzyl-piperidine Oxalate on Coronary Blood Flow in Anesthetized Dogs.

| Expt. No. | Intravenous Dose mg/kg | Coronary Arterial Blood Flow ml/min | | | Duration[2] sec or min | |
|---|---|---|---|---|---|---|
| | | pre-drug | post-drug[1] | % Δ | 50% | 100% |
| 1 | 0.5 | 29 | 32 | +10 | 4 sec | 8 sec |
| | 1 | 26 | 31 | +19 | 8 sec | 20 sec |
| | 2 | 25 | 27 | +8 | 6 sec | 12 sec |
| 2 | 0.5 | 20 | 35 | +75 | 8 sec | 1.8 min |
| | 1 | 15 | 34 | +126 | 8 sec | >7.6 min |
| | 2 | 12 | 33 | +175 | 8 sec | 10 min |
| 3 | 0.5 | 15 | 48 | +220 | 8 sec | 16 sec |
| | 1 | 5 | 41 | +173 | 8 sec | 2.6 min |
| | 2 | 15 | 38 | +153 | 8 sec | 2.2 min |

[1]measured at point of maximal change.
[2]time required for 50% or 100% reduction in maximal change.

TABLE 2

The Effect of 1-[3-(p-fluorobenzyl)propyl]-4-[α-(p-fluorophenyl)]-p-fluorobenzylpiperidine on Coronary Blood Flow in Anesthetized Dogs

| Expt. No. | Intravenous Dose mg/kg | Coronary Arterial Blood Flow ml/min | | | Duration[2] sec or min | |
|---|---|---|---|---|---|---|
| | | pre-drug | post-drug[1] | % Δ | 50% | 100% |
| 1 | 0.5 | 17 | 20 | +17 | 8 sec | 4 min |
| | 1 | 12 | 21 | +75 | 8 sec | 1.2 min |
| | 2 | 12 | 23 | +92 | 8 sec | 1.3 min |
| 2 | 0.5 | 28 | 35 | +25 | 3.2 min | >15 min |
| | 1 | 30 | 41 | +37 | 4.8 min | >12 min |
| | 2 | 30 | 43 | +43 | >8 min | >8 min |
| 3 | 0.5 | 11 | 19 | +72 | 1.7 min | 6.7 min |
| | 1 | 15 | 28 | +87 | 5.5 min | >6.7 min |
| | 2 | 12 | 24 | +100 | 4 sec | >12 min |

[1]measured at point of maximal change.
[2]time required for 50% or 100% reduction in maximal change.

TABLE 3

The Effect of Nitroglycerin on Coronary Blood Flow in Anesthetized Dogs.

| Expt. No. | Intravenous Dose γ/kg | Coronary Arterial Blood Flow ml/min | | | Duration[2] Seconds | |
|---|---|---|---|---|---|---|
| | | pre-drug | post-drug | % Δ | 50% | 100% |
| 1 | 1 | 20 | 24 | +20 | 6 | 12 |
| | 2.5 | 17 | 20 | +17 | 6 | 12 |
| | 5 | 15 | 24 | +60 | 4 | 8 |
| | 10 | 16 | 23 | +43 | 4 | 8 |
| | 20 | 15 | 25 | +108 | 4 | 8 |
| 2 | 1 | 22 | 22 | 0 | — | — |
| | 2.5 | 22 | 25 | +13 | 4 | 8 |
| | 5 | 20 | 27 | +35 | 8 | 16 |
| | 10 | 20 | 26 | +30 | 10 | 16 |
| | 20 | 20 | 27 | +35 | 12 | 16 |
| 3 | 1 | 14 | 11 | −21 | — | — |
| | 2.5 | 11 | 6 | −45 | — | — |
| | 5 | 10 | 15 | +50 | 4 | 8 |
| | 10 | 10 | 14 | +40 | 4 | 8 |
| | 20 | 8 | 13 | +62 | 4 | 8 |
| 4 | 1 | 32 | 32 | 0 | — | — |
| | 2.5 | 32 | 38 | +18 | 4 | 8 |
| | 5 | 32 | 42 | +31 | 6 | 12 |
| | 10 | 27 | 36 | +33 | 4 | 8 |
| | 20 | 25 | 37 | +48 | 6 | 12 |
| 5 | 1 | 32 | 32 | 0 | — | — |
| | 2.5 | 30 | 30 | 0 | — | — |
| | 5 | 30 | 33 | +10 | 2 | 4 |
| | 10 | 30 | 33 | +10 | 2 | 6 |
| | 20 | 28 | 33 | +17 | 4 | 8 |

[1]measured at point of maximal change.
[2]time required for 50% or 100% reduction in maximal change.

TABLE 4

The Effect of Adenosine on Coronary Blood Flow in Anesthetized Dogs.

| Expt. No. | Intravenous Dose γ/kg | Coronary Arterial Blood Flow ml/min | | | Duration[2] seconds | |
|---|---|---|---|---|---|---|
| | | pre-drug | post-drug | % Δ | 50% | 100% |
| 1 | 10 | 27 | 30 | +11 | 4 | 8 |
| | 20 | 26 | 34 | +30 | 2 | 20 |
| | 40 | 26 | 39 | +50 | 8 | 32 |
| | 80 | 27 | 44 | +62 | 12 | 32 |
| | 160 | 26 | 44 | +69 | 16 | 36 |
| 2 | 10 | 26 | 26 | 0 | — | — |
| | 20 | 26 | 26 | 0 | — | — |
| | 40 | 26 | 29 | +11 | 4 | 8 |
| | 80 | 26 | 28 | +7 | 4 | 24 |
| | 160 | 27 | 32 | +18 | 4 | 24 |
| 3 | 10 | 10 | 11 | +10 | 3 | 6 |
| | 20 | 11 | 14 | +27 | 3 | 6 |
| | 40 | 11 | 16 | +45 | 4 | 24 |
| | 80 | 11 | 19 | +72 | 8 | 36 |
| | 160 | 11 | 24 | +118 | 8 | 40 |
| 4 | 10 | 28 | 28 | 0 | — | — |
| | 20 | 28 | 28 | 0 | — | — |
| | 40 | 30 | 33 | +10 | 4 | 8 |
| | 80 | 28 | 33 | +17 | 4 | 8 |
| | 160 | 28 | 40 | +42 | 8 | 40 |
| 5 | 10 | 32 | 36 | +13 | 3 | 6 |
| | 20 | 31 | 38 | +23 | 4 | 8 |
| | 40 | 31 | 42 | +35 | 6 | 24 |
| | 80 | 31 | 49 | +58 | 8 | 30 |
| | 160 | 28 | 53 | +90 | 20 | 72 |

[1]measured at point of maximal change.
[2]time required for 50% or 100% reduction in maximal change.

The compounds of Formula I are generally effective in increasing coronary arterial blood flow in a living mammal. Certain compounds are more effective than others. The compounds of Examples 1 and 2 as the free base or as a pharmaceutically acceptable salt are preferred. The compounds represented by Formula I in association with pharmaceutical carrier or excipient may be presented in a form suitable for oral, parenteral, sublingual, cutaneous, subcutaneous, intraperitoneal, intramuscular, intravenous or intracardial administration or in a form suitable for inhalation. Thus, for example, compositions for oral administration are solid or liquid and can take the form of powders, elixirs, solutions, pills, capsules, tablets, coated tablets, syrups or suspensions. When in admixture with a pharmaceutical vehicle or carrier, the active ingredient usually comprises from about 0.01 to about 75%, normally from about 0.05 to about 25% by weight of the composition.

When the oral route of administration is used, carriers or excipients such as starch, sugar, talc, commonly used synthetic and natural gums and water may be used in such formulations. Binders such as gelatin and lubricants such as sodium stearate may be used to form tablets. Disintegrating agents such as sodium bicarbonate may also be included in tablets.

For parenteral administration, the carrier or excipient can be sterile, parenterally acceptable liquid, e.g., water, or a parenterally acceptable oil, e.g., arachis oil, contained in ampoules.

Although relatively small quantities of the compounds used in this invention, even as low as 0.1 mg., may be used in cases of administration to subjects having a relatively low body weight or to subjects in need of slight increase in coronary arterial blood flow, unit dosages are usually 5 mg. or above, and preferably 25, 50 or 100 mg. or even higher, depending, of course, upon the subject treated and the particular result desired. The usual broader ranges appear to be 1–200 mg. per unit dose. It is only necessary that the active ingredient of the invention constitute an effective amount, i.e., such that a suitable effective dose will be obtained consistent with the dosage form employed. Obviously, several unit dosage forms may be administered at about the same time. The exact individual doses as well as daily dosage in a particular case will, of course, be determined according to well-established principles under the direction of a physician or veterinarian.

It is to be understood that the invention is not to be limited to the exact details of operation, compositions, or procedures shown and described, as obvious modifications and equivalents will be apparent to one skilled in the art and the invention is therefore to be limited only by the scope of the appended claims.

What is claimed is:

1. The method for increasing coronary arterial blood flow in mammals which comprises administering to mammals in need of such treatment a coronary arterial blood flow increasing amount of a compound having the formula:

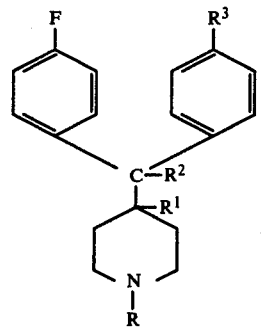

wherein:
R is hydrogen, acetyl, p-fluorobenzoylpropyl, carbamoyl, N-methylcarbamoyl, N,N-dimethylcarbamoyl, phenylcarbamoyl, or N-(ω-morpholinoethyl)carbamoyl;
$R^1$ is hydrogen;
$R^2$ is hydrogen or hydroxy, or
$R^1$ and $R^2$ taken together form a second bond between the carbon atoms bearing $R^1$ and $R^2$;
$R^3$ is hydrogen or fluorine, and
pharmaceutically acceptable acid addition salts thereof.

2. The method of claim 1 wherein R is p-fluorobenzoylpropyl.

3. The method of claim 2 wherein the compound is 1-[3-(p-fluorobenzoyl)propyl]-4-[α-(p-fluorophenyl)-α-hydroxy]-p-fluorobenzylpiperidine.

4. The method of claim 2 wherein the compound is 1-[3-(p-fluorobenzoyl)propyl]-4-[α-(p-fluorophenyl)]-p-fluorobenzylpiperidine.

5. The method of claim 3 wherein the compound is in the form of a pharmaceutically acceptable acid addition salt.

6. The method of claim 4 wherein the compound is in the form of a pharmaceutically acceptable acid addition salt.

7. The method of claim 5 wherein the compound is 1-[3-(p-fluorobenzoyl)propyl]-4-[α-(p-fluorophenyl)-α-hydroxy]-p-fluorobenzylpiperidine oxalate.

* * * * *